US00PP20251P2

(12) United States Plant Patent
Smith

(10) Patent No.: US PP20,251 P2
(45) Date of Patent: Sep. 1, 2009

(54) ***CHRYSANTHEMUM* PLANT NAMED 'FROSTY YOIGLOO'**

(50) Latin Name: *Chrysanthemum×morifolium*
Varietal Denomination: Frosty Yoigloo

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,250

(22) Filed: Jun. 16, 2008

(51) Int. Cl.
*A01H 5/00* (2006.01)

(52) U.S. Cl. ..... Plt./288
(58) Field of Classification Search ..... Plt./288
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Frosty Yoigloo', characterized by its upright, outwardly spreading and mounding plant habit; freely branching habit; dense and full plant habit; uniform and freely flowering habit; decorative-type inflorescences with white-colored ray florets; and natural season flowering about September 24$^{th}$ in the Northern Hemisphere.

1 Drawing Sheet

Botanical designation: *Chrysanthemum×morifolium.*
Cultivar denomination: 'Forsty Yoigloo'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum,* and hereinafter referred to by the name 'Frosty Yoigloo'.

The objective of the breeding program is to create new perennial garden-type *Chrysanthemum* cultivars having uniformly rounded plant habit, inflorescences with desirable inflorescence forms, attractive floret colors and good garden performance.

The new *Chrysanthemum* originated from a cross-pollination made by the Inventor in December, 2002, in Salinas, Calif. of a proprietary seedling selection of *Chrysanthemum×morifolium* identified as code number 98-M305, not patented, as the female, or seed, parent with *Chrysanthemum×morifolium* 'Mei Kyo', not patented, as the male, or pollen, parent. The new *Chrysanthemum* was discovered and selected by the Inventor as a single flowering plant within the progeny of the stated cross-pollination in a controlled greenhouse environment in Alva, Fla. in October, 2003.

Asexual reproduction of the new *Chrysanthemum* by vegetative cuttings was first conducted in a controlled greenhouse environment in Alva, Fla. in January, 2004. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Frosty Yoigloo'. These characteristics in combination distinguish 'Frosty Yoigloo' as a new and distinct garden *Chrysanthemum* cultivar:

1. Upright, outwardly spreading and uniformly mounded plant habit.
2. Freely branching habit; dense and full plant habit.
3. Uniform and freely flowering habit.
4. Decorative-type inflorescences.
5. White-colored ray florets.
6. Natural season flowering occurs about September 24$^{th}$ in the Northern Hemisphere.

In side-by-side comparisons conducted in Alva, Fla., plants of the new *Chrysanthemum* differed from plants of the female parent selection in the following characteristics:

1. Plants of the new *Chrysanthemum* flowered a few days later than plants of the female parent selection when grown under natural season conditions.
2. Plants of the new *Chrysanthemum* had smaller inflorescences than plants of the female parent selection.
3. Plants of the new *Chrysanthemum* and the female parent selection differed in ray floret color as plants of the female parent selection had lavender-colored ray florets.

In side-by-side comparisons conducted in Alva, Fla., plants of the new *Chrysanthemum* differed from plants of the male parent, 'Mei Kyo', in the following characteristics:

1. Plants of the new *Chrysanthemum* were smaller than plants of 'Mei Kyo'.
2. Plants of the new *Chrysanthemum* flowered about one month earlier than plants of 'Mei Kyo' when grown under natural season conditions.
3. Plants of the new *Chrysanthemum* and 'Mei Kyo' differed in ray floret color as plants of 'Mei Kyo' had pale lavender-colored ray florets.

Plants of the new *Chrysanthemum* can be compared to plants of *Chrysanthemum×morifolium* 'MN95-157-6', not patented. In side-by-side comparisons conducted in Alva, Fla., plants of the new *Chrysanthemum* differed from plants of 'MN95-157-6' in the following characteristics:

1. Plants of the new *Chrysanthemum* were more mounding than plants of 'MN95-157-6'.
2. Plants of the new *Chrysanthemum* were more freely branching than plants of 'MN95-157-6'.
3. Plants of the new *Chrysanthemum* had smaller inflorescences with more ray florets than plants of 'MN95-157-6'.
4. Plants of the new *Chrysanthemum* and 'MN95-157-6' differed in inflorescence form as plants of 'MN95-157-6' had daisy-type inflorescences.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Frosty Yoigloo' grown in a container.

The photograph at the top of the sheet is a close-up view of typical inflorescences of 'Frosty Yoigloo'.

DETAILED BOTANICAL DESCRIPTION

The aforementioned photographs and following observations and measurements describe plants grown in Alva, Fla. during the late spring and summer in a polycarbonate-covered greenhouse and under conditions and practices which approximate those generally used in commercial garden *Chrysanthemum* production. During the production of the plants, day temperatures averaged 32° C. and night temperatures averaged 21° C. Plants were grown in 15-containers under short day/long night conditions. Plants were ten weeks from planting when the photographs and description were taken. In the following description, color references are made to The Royal Horticultural Society Colour Chart, 1995 Edition, except where general terms of ordinary dictionary significance are used.

Botanical classification: *Chrysanthemum×morifolium* 'Frosty Yoigloo'.

Parentage:

*Female, or seed, parent.*—Proprietary seedling selection of *Chrysanthemum×morifolium* identified as code number 98M305, not patented.

*Male, or pollen, parent.*—*Chrysanthemum×morifolium* 'Mei Kyo', not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial decorative-type garden *Chrysanthemum*. Stems upright and outwardly spreading giving a uniformly mounded appearance to the plant. Freely branching habit, about seven to eight lateral branches each with multiple secondary branches; pinching is not required; dense and full plant habit. Strong and vigorous growth habit.

*Plant height.*—About 24 cm.

*Plant width.*—About 32 cm.

*Lateral branches.*—Length: About 20 cm. Diameter: About 4 mm. Internode length: About 1.1 cm. Strength: Strong. Texture: Pubescent; longitudinally ridged. Color: Close to 148B.

*Leaves.*—Arrangement: Alternate, simple. Length: About 5.5 cm. Width: About 4.7 cm. Apex: Broadly acute. Base: Truncate with attenuate tendencies. Margin: Palmately lobed, sinuses between lateral lobes mostly parallel. Texture, upper and lower surfaces: Pubescence; veins prominent on lower surface. Color: Developing and fully expanded foliage, upper surface: Close to 147A; venation, close to 147B. Developing and fully expanded foliage, lower surface: Close to 147B; venation, close to 147C. Petiole: Length: About 1.8 cm. Diameter: About 3 mm. Texture, upper and lower surfaces: Pubescent. Color, upper and lower surfaces: Close to 147C.

Inflorescence description:

*Appearance.*—Decorative-type inflorescence form with obovate-shaped ray florets. Inflorescences borne on terminals above foliage. Disc and ray florets arranged acropetally on a capitulum. Inflorescences fragrant, pungent.

*Flowering response.*—Under natural season conditions, plants flower about September 24$^{th}$ in the Northern Hemisphere.

*Postproduction longevity.*—Inflorescences maintain good color and substance for about four weeks in an outdoor nursery. Inflorescences persistent.

*Quantity of inflorescences.*—About 22 to 24 inflorescences develop per lateral branch.

*Inflorescence bud.*—Height: About 1 cm. Diameter: About 9 mm. Shape: Oblate. Color: Close to 155A.

*Inflorescence size.*—Diameter: About 3.6 cm. Depth (height): About 1.2 cm. Disc diameter: About 2 mm. Receptacle diameter: About 1.5 cm. Receptacle height: About 4 mm. Receptacle color: Close to 148A to 148B.

*Ray florets.*—Shape: Obovate. Orientation: Initially upright, then about 90° from vertical. Aspect: Initially incurved, then mostly flat. Length: About 1.7 cm. Width: About 5 mm. Apex: Emarginate. Base: Acute. Margin: Entire. Texture, upper and lower surfaces: Smooth, glabrous; velvety; longitudinally ribbed. Number of ray florets per inflorescence: About 118 arranged in about nine to ten whorls. Color: When opening, upper surface: Close to 157B. When opening, lower surface: Close to 157D. Fully opened, upper and lower surfaces: Close to 155D.

*Disc florets.*—Shape: Tubular, elongated. Length: About 4 mm to 5 mm. Diameter: About 1 mm. Number of disc florets per inflorescence: About ten. Color, immature: Apex: Close to 7A. Mid-section: Close to 157B. Base: Close to 157D. Color, mature: Apex: Close to 17B. Mid-section: Close to 17C. Base: Close to 157D.

*Phyllaries.*—Number of phyllaries per inflorescence: About 14 arranged in about two or three whorls. Length: About 6 mm. Width: About 2 mm. Shape: Elliptical. Apex: Acute. Base: Truncate. Texture, upper surface: Smooth, glabrous. Texture, lower surface: Pubescent. Color, upper surface: Close to 146B. Color, lower surface: Close to 147B.

*Peduncles.*—Length, terminal peduncle: About 3.5 cm. Length, fourth peduncle: About 2.6 cm. Diameter, terminal peduncle: About 1.5 mm. Angle: Mostly upright to 30° to 45° from vertical. Strength: Strong. Texture: Pubescent. Color: Close to 148C.

*Reproductive organs.*—Androecium: Stamen number: About five per floret. Filament length: About 2 mm. Filament color: Close to 17D. Anther length: About 2.5 mm. Anther shape: Oblong. Anther color: Close to 17C. Pollen amount: Scarce. Pollen color: Close to 17C. Gynoecium: Pistil length: About 5 mm. Stigma shape: Bi-parted. Stigma color: Close to 5B. Style length: About 3 mm. Style color: Close to 145C. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Frosty Yoigloo' as illustrated and described.

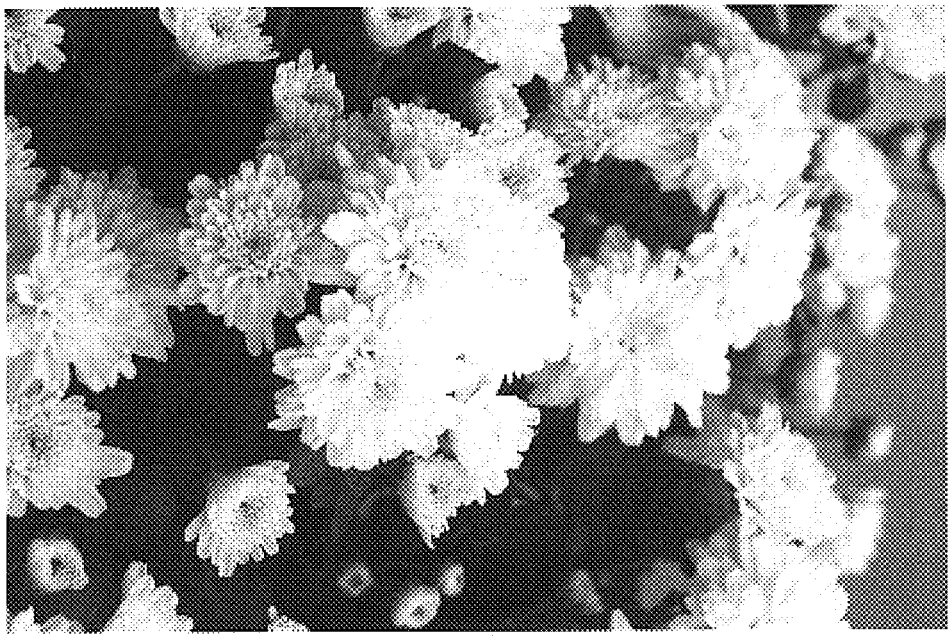
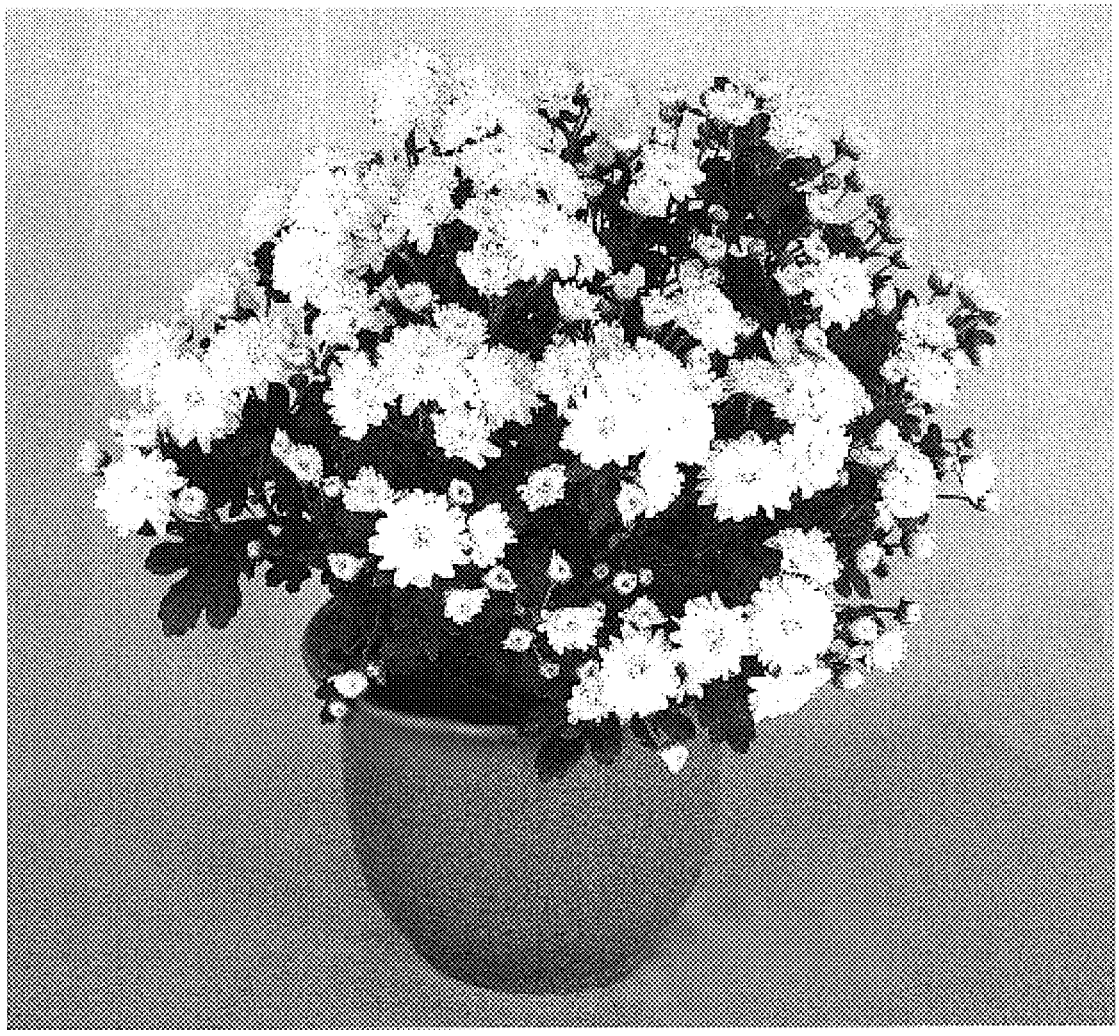

* * * * *